United States Patent
Choi et al.

(10) Patent No.: US 9,180,198 B2
(45) Date of Patent: Nov. 10, 2015

(54) SLOW-RELEASE CILOSTAZOL TABLET HAVING AN IMPROVED ELUTION RATE AND MINIMAL SIDE EFFECTS

(75) Inventors: Youn-Woong Choi, Ansan-si (KR); Byung-Gu Min, Seoul (KR); Sang-Min Cho, Siheung-si (KR)

(73) Assignee: KOREA UNITED PHARM, INC., Seoul (KR)

( * ) Notice: Subject to any disclaimer, the term of this patent is extended or adjusted under 35 U.S.C. 154(b) by 131 days.

(21) Appl. No.: 13/395,926

(22) PCT Filed: Sep. 23, 2009

(86) PCT No.: PCT/KR2009/005420
§ 371 (c)(1),
(2), (4) Date: Mar. 14, 2012

(87) PCT Pub. No.: WO2011/037281
PCT Pub. Date: Mar. 31, 2011

(65) Prior Publication Data
US 2012/0172395 A1    Jul. 5, 2012

(51) Int. Cl.
| | | |
|---|---|---|
| *A61K 9/22* | (2006.01) | |
| *A61K 47/38* | (2006.01) | |
| *A61K 9/20* | (2006.01) | |
| *A61K 31/4709* | (2006.01) | |
| *A61K 47/32* | (2006.01) | |

(52) U.S. Cl.
CPC ............... *A61K 47/38* (2013.01); *A61K 9/2027* (2013.01); *A61K 9/2054* (2013.01); *A61K 9/2095* (2013.01); *A61K 31/4709* (2013.01); *A61K 47/32* (2013.01)

(58) Field of Classification Search
None
See application file for complete search history.

(56) References Cited

U.S. PATENT DOCUMENTS

| | | | | |
|---|---|---|---|---|
| 6,245,351 | B1 * | 6/2001 | Nara et al. | ..................... 424/461 |
| 7,144,585 | B1 * | 12/2006 | Mukai et al. | .................. 424/452 |
| 2005/0096296 | A1 * | 5/2005 | Fikstad et al. | .................. 514/58 |
| 2005/0106245 | A1 | 5/2005 | Yuso | |
| 2008/0268044 | A1 | 10/2008 | Appleby et al. | |

FOREIGN PATENT DOCUMENTS

| | | |
|---|---|---|
| KR | 2004-0084930 A | 10/2004 |
| KR | 2007-0021830 A | 2/2007 |
| KR | 2007-0024254 A | 3/2007 |
| KR | 2008-0074178 A | 8/2008 |

OTHER PUBLICATIONS

International Search Report (in Korean with English translation) for PCT/KR2009/005420 mailed May 25, 2010; ISA/KR.

* cited by examiner

*Primary Examiner* — Snigdha Maewall
(74) *Attorney, Agent, or Firm* — Harness, Dickey & Pierce, PLC

(57) ABSTRACT

Provided is a slow-release tablet including cilostazol as a pharmacologically active component, which is efficacious in suppressing aggregation of blood platelets and promoting vascular relaxation by inhibiting phosphodiesterase types. The slow-release cilostazol tablet has an extended elution time so that the slow-release cilostazol tablet can be taken once daily for convenience of drug use, and minimizes the manifestation of headache which is one side effect caused when women, the elderly and children take conventional cilostazol preparations so that the convenience of drug use can be improved. Also, the slow-release cilostazol tablet exhibits a stable elution pattern with no variation in elution rate according to changes in pH in the stomach and intestines, as well as an effect of delaying the release of a drug, using a mixture of hydroxypropyl methylcellulose and a carbomer as a release-controlling polymer.

7 Claims, 5 Drawing Sheets

SLOW-RELEASE CILOSTAZOL TABLET HAVING AN IMPROVED ELUTION RATE AND MINIMAL SIDE EFFECTS

CROSS-REFERENCE TO RELATED APPLICATION

This application is a 371 U.S. National Stage of International Application No. PCT/KR2009/005420, filed Sep. 23, 2009, the disclosure of which is herein incorporated by reference in its entirety.

TECHNICAL FIELD

The present invention relates to a slow-release tablet including cilostazol as a pharmacologically active component which is prepared with a release-controlling polymer, and, more specifically, to a slow-release cilostazol tablet which is capable of being administered once daily and reducing side effects, such as headache, heavy headedness and tachycardia, of the cilostazol by controlling a stable elution rate of cilostazol according to changes in pH to, so that the convenience of tablet use can be improved.

BACKGROUND ART

As a quinolinone-based compound, cilostazol (6-[4-(cyclohexyl-1H-tetrazol-5-yl)butoxy]-3,4-dihydro-2(1H)-quinolinone: Chemical formula 1) has an efficacy in controlling aggregation of blood platelets and promoting vascular relaxation by inhibiting phosphodiesterase types. Also, cilostazol is known to be useful in preventing diseases such as arteriosclerosis by suppressing the growth of vascular smooth muscle cells that have migrated to vascular endothelial cells.

Chemical formula 1

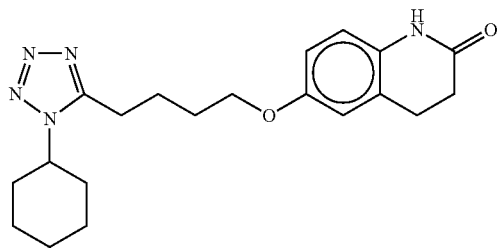

Cilostazol functions to suppress the primary aggregation of blood platelets caused by ADP, epinephrine and the like in blood platelets isolated from a mouse, a rat, a rabbit, a dog and a human and dissociate a blood platelet aggregate. Also, cilostazol functions to suppress the aggregation of blood platelets induced by ADP and collagen when administered orally to a beagle, and also suppress the aggregation of blood platelets induced by ADP, collagen, arachidonic acid and epinephrine in blood platelets isolated from a patient with a chronic arterial occlusive disease (Buerger's disease, arteriosclerosis obliterans, diabetic peripheral angiopathy, etc.) when administered orally to the patient. The effect of cilostazol to suppress the blood platelet aggregation is manifested immediately after administration of the cilostazol, and maintained by repeated administration of the cilostazol. When the administration of the cilostazol is suspended, suppressed aggregation of the blood platelets returns to its original level with a decrease in its concentration in blood plasma without a rebound phenomenon (rise in aggregation).

The action mechanism of cilostazol is as follows. Cilostazol functions to suppress the release of serotonin from rabbit blood platelets, but has no effect on migration of serotonin and adenosine into the blood platelets. Also, the cilostazol functions to suppress the aggregation of blood platelets caused by thromboxane A2 (TXA2) without affecting an arachidonic acid metabolism in the blood platelets. This indicates that the cilostazol functions to inhibit cAMP-PDE (cyclic AMP phosphodiesterase) activity in blood platelets and vascular smooth muscles, thereby exhibiting an anti-blood platelet action and a vascular dilatation action.

Conventional cilostazol preparations have a disadvantage in that they have poor patient compliance when administered twice daily. Also, immediate-release cilostazol preparations have a disadvantage in that the drug is rapidly and irregularly released when administered orally. Thus, it is known that these cilostazol preparations cause side effects such as headache, heavy headedness and tachycardia with a sudden increase in cilostazol concentration in blood (see Am J Cardiol 2001; 87(suppl): 28D-33D and US 2002/0058066 A1). Since the cilostazol is poorly water-soluble and also has a reduced absorption rate in the lower small intestine, a conventional release-controlling preparation using the cilostazol has a disadvantage in that its bioavailability may be deteriorated as a whole. Also, WO 2000/57881 discloses a method of improving an absorption rate of cilostazol in the lower small intestine using a preparation in which cilostazol in a fine powder form is dispersed and/or dissolved together with a dispersing agent and/or a solubilizing agent.

Conventional cilostazol tablets cause side effects such as headache, tachycardia and heavy headedness due to a high elution rate immediately after their administration. Therefore, there is the high necessity for cilostazol prepared into a slow-release tablet, and there is a need to develop a slow-release cilostazol tablet which simply delays the release of a drug and also exhibits a stable elution rate when taken once daily.

DISCLOSURE

Technical Problem

The present invention is designed to solve the problems of the prior art, and therefore it is an object of the present invention to provide a preparation which has an advantage of a water-soluble polymer in a matrix type which has been used in conventional slow-release preparations, and also suppresses the manifestation of side effects as the release of a drug is uniformly and precisely controlled by a separate action of a control system in the intestines so that a constant drug concentration in blood can be maintained in vivo.

Technical Solution

According to one exemplary embodiment of the present invention, a slow-release cilostazol tablet including cilostazol, a release-controlling polymer, a binder, a filler and a lubricant include a mixture of one or more components selected from the group consisting of hydroxypropyl methylcellulose, a carbomer, hydroxypropyl cellulose, methylcellulose, polyvinyl pyrrolidone and polyvinyl alcohol as a release-controlling polymer.

According to another exemplary embodiment of the present invention, the release-controlling polymer included in the slow-release cilostazol tablet may be a mixture of the hydroxypropyl cellulose and the carbomer.

According to still another exemplary embodiment of the present invention, the mixture of the hydroxypropyl cellulose and the carbomer included in the slow-release cilostazol tablet may be present at a content of 25 to 50% by weight, based on the total weight of the tablet.

According to still another exemplary embodiment of the present invention, the release-controlling polymer, hydroxypropyl methylcellulose, included in the slow-release cilostazol tablet may have a viscosity of 80,000 cps to 120,000 cps.

According to yet another exemplary embodiment of the present invention, the hydroxypropyl methylcellulose and the carbomer included in the slow-release cilostazol tablet may be mixed at a mixing ratio of 1:1 to 20:1.

Advantageous Effects

The slow-release cilostazol tablet according to the present invention has an extended elution time so that the slow-release cilostazol tablet can be taken once daily for convenience of drug use, and minimizes the manifestation of headache which is one side effect of the conventional cilostazol preparations. Also, the slow-release cilostazol tablet according to the present invention maintains a constant elution rate even in changes in pH in the stomach and intestines.

BEST MODE

Figure 1:
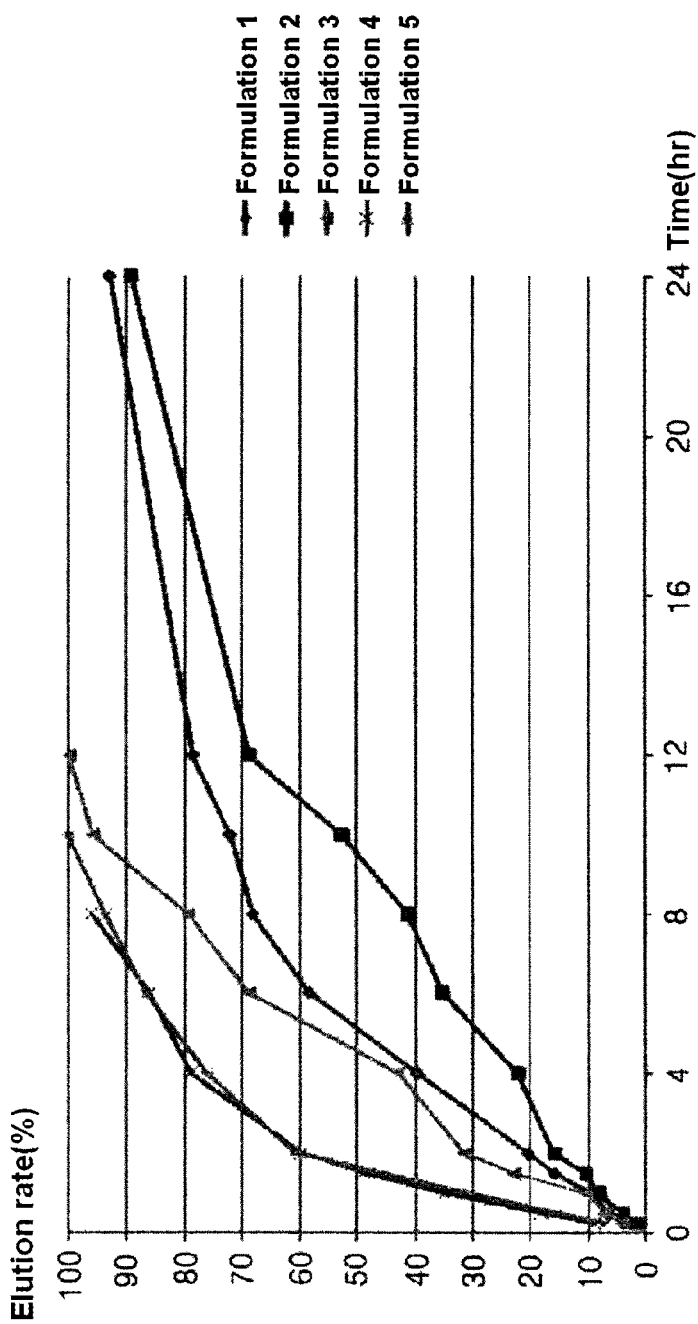
FIG. 1 shows the elution test results of Formulations 1 to 5 prepared in Example 1 and Comparative Example 1 according to the present invention.
Figure 2:
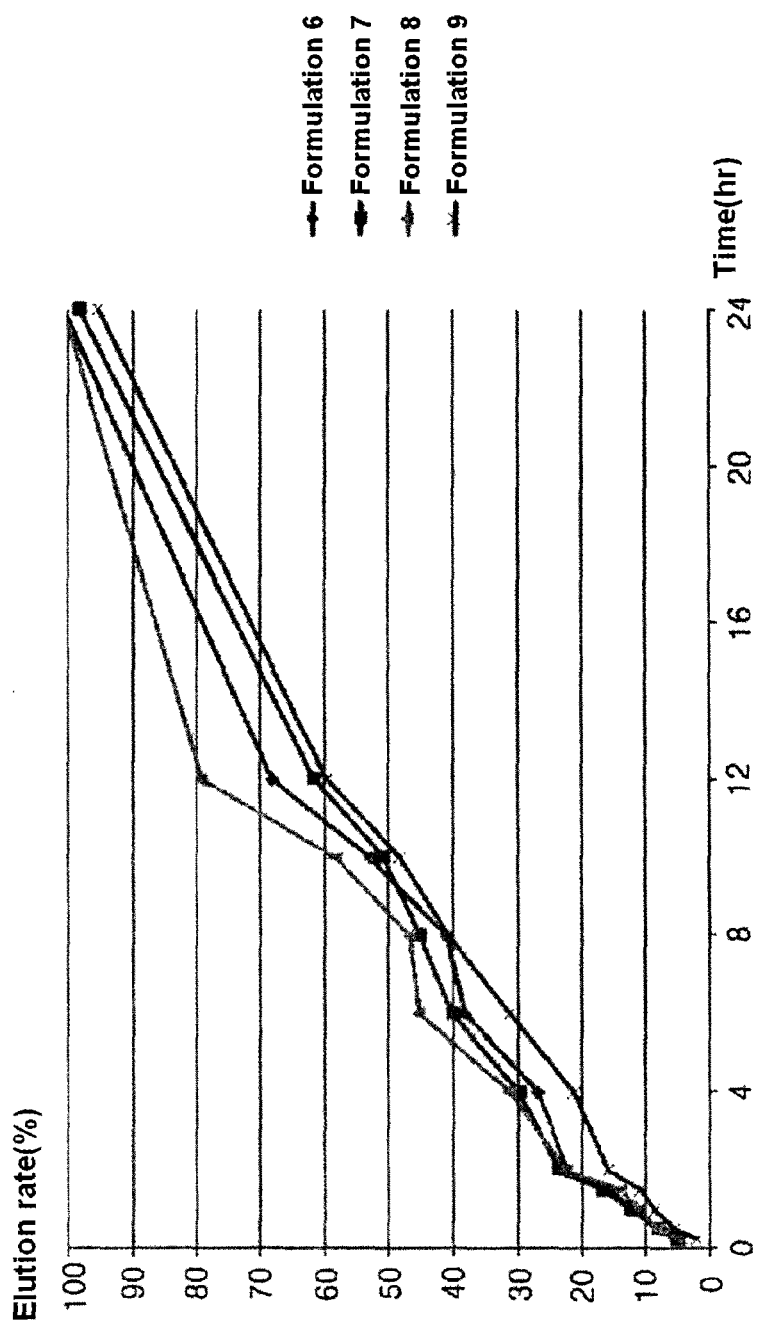
FIG. 2 shows the elution test results of Formulations 6 to 9 prepared in Example 2 according to the present invention.
Figure 3:
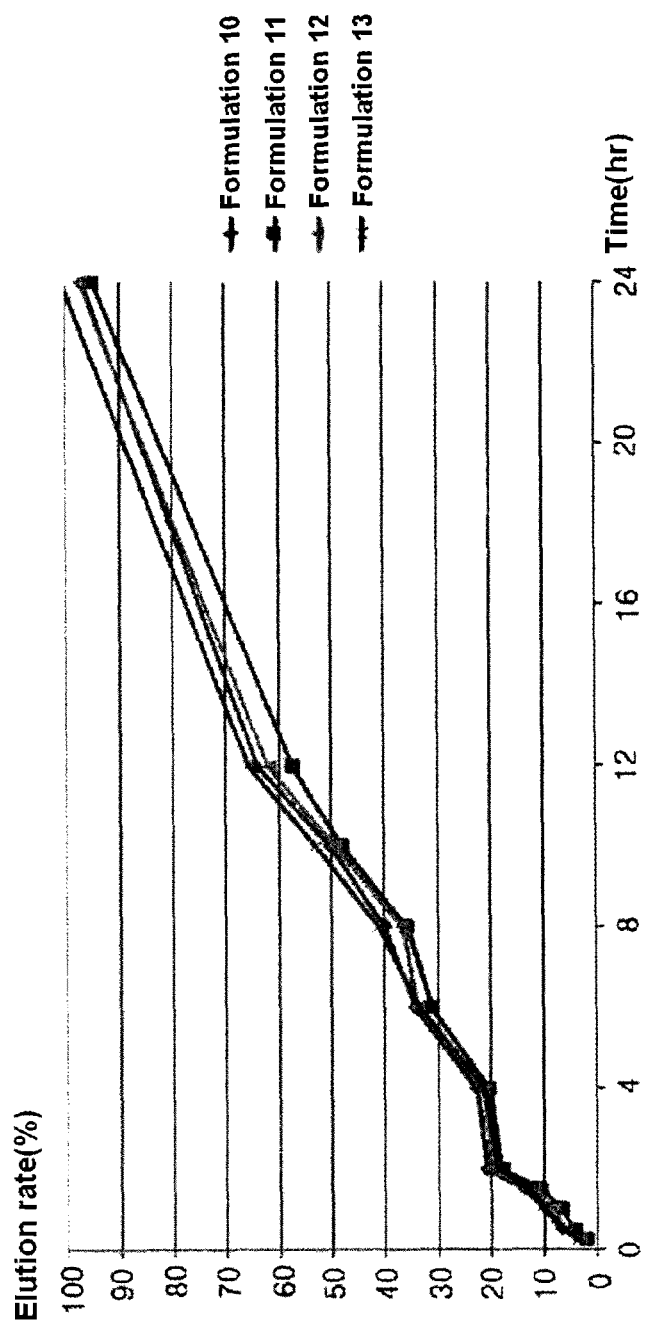
FIG. 3 shows the elution test results of Formulations 10 to 13 prepared in Example 3 according to the present invention.
Figure 4:
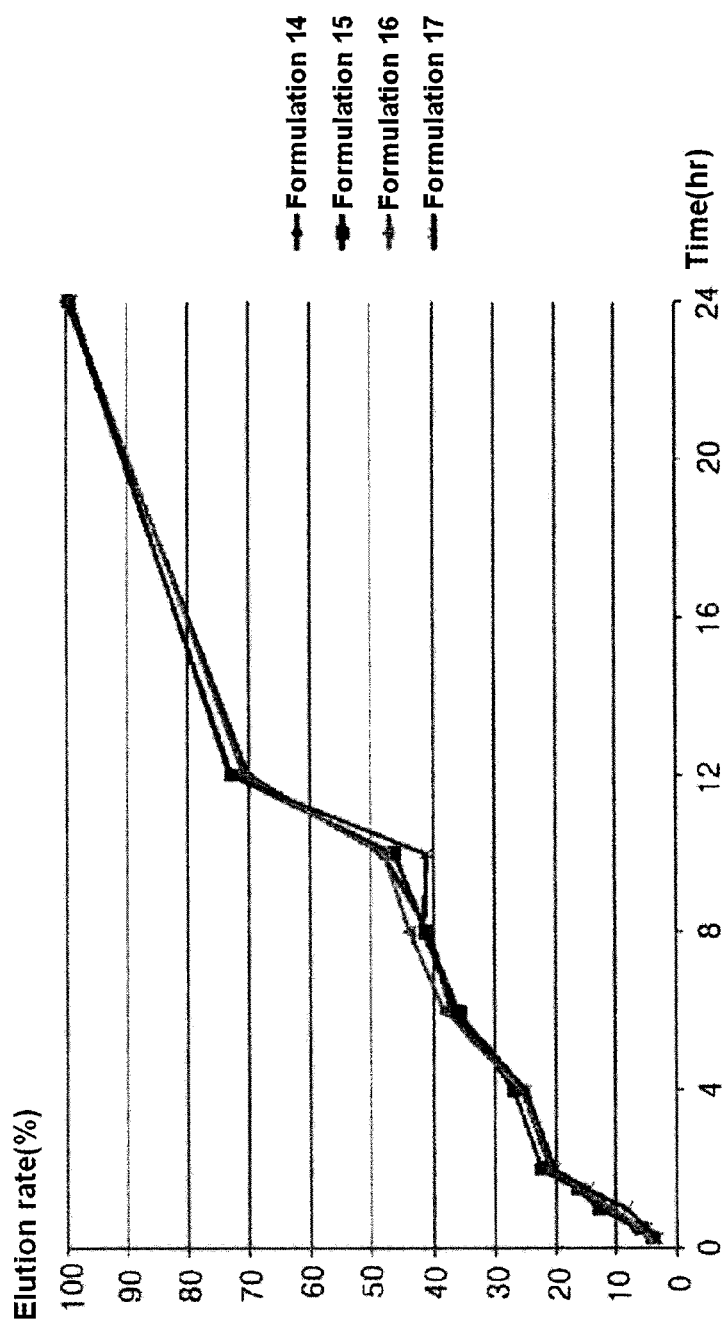
FIG. 4 shows the elution test results of Formulations 14 to 17 prepared in Example 4 according to the present invention.
Figure 5:
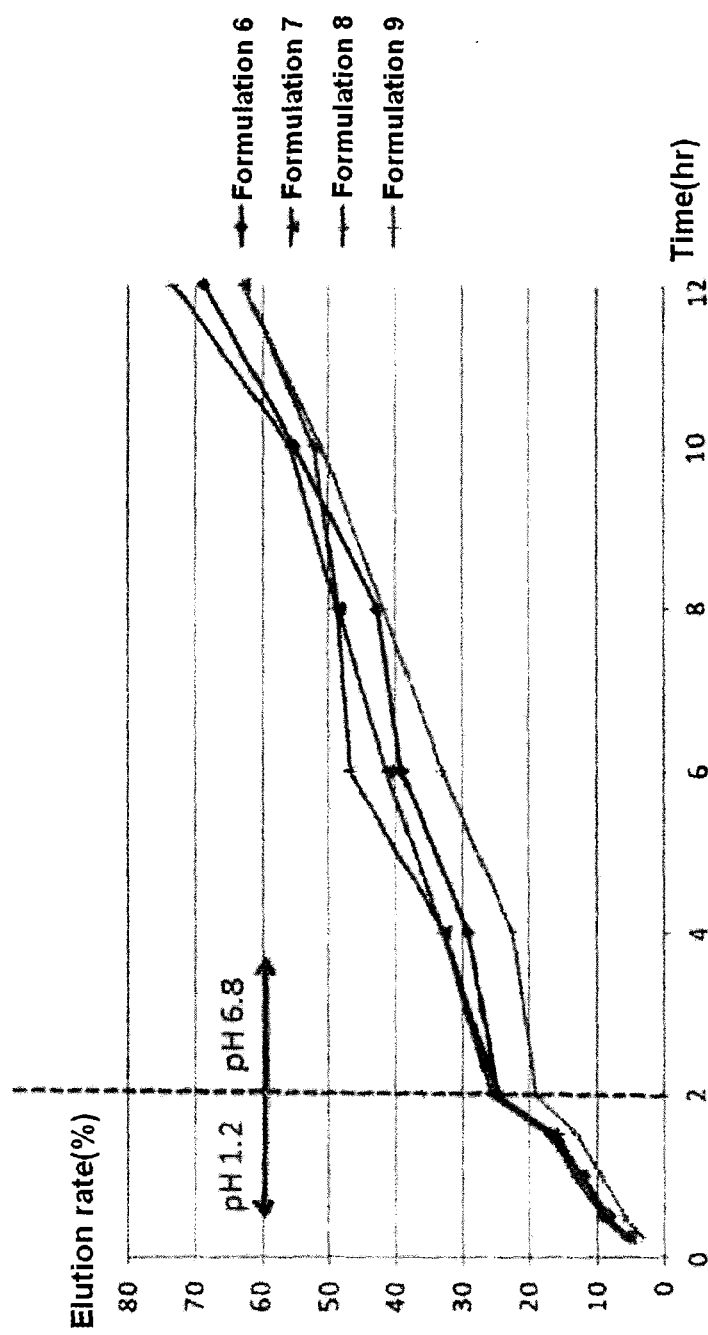
FIG. 5 shows the results obtained by measuring elution rates of Formulations 6 to 9 of Example 5 according to changes in pH according to the present invention.

The present invention relates to a slow-release tablet (i.e., a sustained-release tablet) including cilostazol. More particularly, the present invention provides a slow-release cilostazol tablet which has an extended elution time so that the slow-release cilostazol tablet can be taken once daily, functions to control the release of a drug using a water-soluble matrix system and shows improved convenience of drug use when women, the elderly and children take the drug by regulating the release of the drug according to changes in pH to uniformly and precisely control the intake of the drug in the stomach and intestines, thereby suppressing the manifestation of side effects of cilostazol.

The slow-release cilostazol tablet according to the present invention includes cilostazol, a release-controlling polymer, a binder, a filler and a lubricant.

All of pharmaceutically available polymers may be used as the release-controlling polymer. Examples of the release-controlling polymer may be a mixture of one or more components selected from the group consisting of a cellulose derivative such as hydroxypropyl methylcellulose, methylcellulose, ethylcellulose, hydroxypropyl cellulose or sodium carboxylmethylcellulose, a propylene oxide and a derivative thereof, polyvinyl pyrrolidone (molecular weight: 90 Da, Trade name: Povidone K-90), polyethylene glycol, polyvinyl alcohol, polyvinylacetate, polyvinylacetate phthalate, polymethacrylate, a polymer of polymethacrylate (commercially available as Eudragit, polyacrylic acid), a derivative of polymethacrylate (representatively, a carbomer), glycerol monostearate and poloxamer. Preferably, a mixture of one or more components selected from the group consisting of hydroxypropyl methylcellulose, a carbomer, hydroxypropyl cellulose, methylcellulose, polyvinyl pyrrolidone and polyvinyl alcohol may be used. More preferably, a mixture of hydroxypropyl cellulose and a carbomer may be used.

The release-controlling polymer included in the slow-release cilostazol tablet according to the present invention may be present at a content of 25% to 50% by weight, based on the total weight of the tablet. When the content of the release-controlling polymer is less than 25% by weight, the side effects may be caused due to a short release time of cilostazol and an increase in elution rate per time unit, whereas the remedial results may be insufficient due to a long release time of cilostazol and a decrease in elution rate per time unit when the content of the release-controlling polymer exceeds 50% by weight.

The slow-release tablet having an effect of delaying the elution of a pharmacologically active component may be prepared by mixing with a release-controlling polymer. In general, methylcellulose, ethylcellulose, hydroxymethylcellulose and polyvinyl pyrrolidone may be used as the release-controlling polymer.

The present inventors have found that, when a slow-release tablet is prepared by mixing a carbomer with a typical release-controlling polymer, the slow-release tablet shows a long elution time and a stable drug elution pattern, compared to a slow-release tablet prepared using a single-component release-controlling polymer. Also, they have found that an elution pattern can be regulated by regulating a weight ratio of a release-controlling polymer rather than the carbomer and another carbomer.

Since the rapid elution of cilostazol may cause tachycardia, heavy headedness or headache, one important factor is to maintain/control a constant elution rate for the slow-release tablet. Hydroxypropyl methylcellulose may form a matrix in a tablet to prevent rapid elution of the pharmacologically active component, thereby securing a long elution time. Also, the hydroxypropyl methylcellulose shows a stable elution pattern, compared to other release-controlling polymers.

The slow-release tablet including the pharmacologically active component may swell when the pharmacologically active component is eluted. In this case, when the matrix of the release-controlling polymer is not solidly formed, the matrix may be partially eroded, and thus the tablet may disintegrate, which leads to rapid drug release, causing a patient to suffer from headache or flush. In order to solve these problems, a mixture of high-viscosity hydroxypropyl methylcellulose and a carbomer was used as the release-controlling polymer in the present invention. As the release-controlling polymer, the carbomer is present in a sol state in the stomach which is maintained at an acid condition so that the release of a drug can be maintained by a hydroxypropyl methylcellulose system. In addition, the carbomer is present in a hydrogel state in the small intestine which is maintained at an alkaline condition so that the release of the drug can be controlled. When the carbomer is used together with hydroxypropyl methylcellulose, the carbomer functions to solidly form a matrix in the slow-release tablet, maintain the shape of the matrix due to swelling of the tablet, and prevent erosion of the tablet by maintaining a constant matrix in the tablet, which makes it possible to maintain a constant elution rate.

The hydroxypropyl methylcellulose used herein may be hydroxypropyl methylcellulose having a viscosity of 80,000 cps to 120,000 cps, preferably 90,000 cps to 110,000 cps. When the viscosity of the hydroxypropyl methylcellulose is less than 80,000 cps, a large amount of hydroxypropyl methylcellulose is required, which leads to an increase in size of the tablet. On the other hand, when the viscosity of the hydroxypropyl methylcellulose exceeds 120,000 cps, cilostazol may not be uniformly mixed. At such a viscosity, a product having consistent particle grind uniformity, excellent dispersibility and a good physical form may be used as the hydroxypropyl methylcellulose.

The hydroxypropyl methylcellulose and the carbomer included in the slow-release cilostazol tablet according to the present invention may be mixed in a weight ratio of 1:1 to 20:1. When the weight ratio is less than 1:1, a matrix may not be easily formed in the tablet, and thus the delay of drug release may not work properly. On the other hand, when the weight ratio exceeds 20:1, an elution rate of cilostazol at an alkaline condition may be decreased, and the cilostazol and the release-controlling polymer may not be mixed uniformly. Preferably, the cilostazol and the release-controlling polymer may be mixed at a weight ratio of 1.5:1 to 10:1.

The slow-release cilostazol tablet according to the present invention shows a constant elution rate according to changes in pH. An orally administered slow-release tablet is sustained in the human body for at least 8 hours. In particular, the slow-release tablet has to maintain a constant elution rate according to changes in pH since the changes in pH are very high in the stomach and small intestine in which the slow-release tablet is sustained for a long time. The slow-release cilostazol tablet according to the present invention may maintain a constant elution rate at pH 1.2 (e.g., in an artificial gastric juice) and pH 6.8 (e.g., in an artificial intestinal juice).

The binder used herein may include a polyvinyl pyrrolidone (including one having a molecular weight of 30 Da, Trade name: Povidone K-30) or a derivative thereof (PVP), which may be generally used for oral administration, a copolymer (co-pvp) of vinyl pyrrolidone and a vinyl derivative, and a starch, but the present invention is not limited thereto. The polyvinyl pyrrolidone (Povidone K-30) having a molecular weight of 30 Da or the copolymer (co-pvp) of vinyl pyrrolidone and a vinyl derivative may be the most widely used, and a mixture of the polyvinyl pyrrolidone and the copolymer may be used herein. The binder may be included at a content of 3 to 10% by weight, based on the total weight of the tablet. When the binder is added at a content of less than 3% by weight, it is difficult to perform a tableting process due to a low bonding force. On the other hand, when the binder is added at a content of greater than 10% by weight, it is difficult to regulate a constant elution rate of the drug. However, the present invention is not limited thereto.

The filler used herein may include an adhesive generally used for pharmaceutical purposes. Such an adhesive that may be used herein may include lactose, sugar, mannitol, sorbitol, and a mixture thereof. As necessary, the filler may include a stabilizing agent and a preservative. The filler may be included at a content of 10 to 30% by weight, based on the total weight of the tablet, but the present invention is not limited thereto.

Magnesium stearate, fumed silica ($SiO_2$), amorphous fumed silica, talc or a mixture thereof may be added as the lubricant used in the present invention, but the present invention is not limited thereto. The lubricant may be included at a content of 1 to 5% by weight, based on the total weight of the tablet. When the lubricant is added at a content of less than 1% by weight, a tablet may not be easily formed. On the other hand, when the lubricant is added at a content of greater than 5% by weight, the coating of lubricant granules may affect an elution pattern of cilostazol. However, the present invention is not limited thereto.

Hereinafter, the present invention will be described in further detail with reference to the following Examples and Comparative Examples. However, the Examples are given by way of illustration only, and not intended to limit the scope of the present invention.

Mode for Invention

Elution Rate Experiment

An elution test was performed according to an elution test method described in Korean Herbal Pharmacopoeia ($7^{th}$ edition). A phosphate buffer (pH 7.8) was used as an elution solution, and a paddle method was used as an elution method, and performed at a stirring speed of 100 rpm and an elution temperature of 37±0.5° C. in 900 ml of the elution solution. 5 ml of samples were taken at time points of 0, 5, 10, 15, 30, 45 and 60 minutes, and an equivalent amount of an elution solution was added to the samples. The analysis conditions were as follows. The solutions obtained from the elution test were filtered through a 0.45 µm membrane filter, and the resulting filtrates were quantified by HPLC using aceclopenac. An assay wavelength was 277 nm, a mobile phase was a solution of acetonitrile and a phosphate buffer (pH 7.4) (volume ratio: 68:32), a flow rate was 1.0 ml/min, and C18 ODS was used as a column.

Example 1

Formulations listed in the following Table 1 were used to prepare slow-release tablets using the following method. First, Povidone K-30 and a carbomer (50%) were dispersed and dissolved in ethanol to prepare a binder solution. Next, cilostazol, microcrystalline cellulose, a carbomer (50%) and hydroxypropyl methylcellulose were thoroughly mixed using a speed mixer, and then made into wet granules in a cylindrical granulating machine using the binder solution. The prepared granules were dried in a drying oven (40° C.) for 12 hours, and passed through a 40-mesh sieve. Thereafter, light anhydrous silicic acid and magnesium stearate were further mixed with the sieved half-finished product, and formed into tablets so that one tablet could amount to the weight as listed in the following Table 1. An elution test was performed on the slow-release cilostazol tablets having constant contents as prepared in the following Examples according to the elution test method described in Korean Herbal Pharmacopoeia. An aqueous solution of 0.5 W/W % sodium lauryl sulfate was used as an elution solution, and a paddle method was used as an elution method, and performed at a stirring speed of 75 rpm and an elution temperature of 37±0.5° C. in 900 ml of an elution solution. 5 ml of samples were taken at time points of 15, 30, 60, 90, 120, 240, 360, 480, 600 and 720 minutes, and an equivalent amount of an elution solution was added to the samples. The analysis conditions were as follows. The solutions obtained from the elution test were filtered through a 0.45 μm membrane filter, and the resulting filtrates were quantified by HPLC using cilostazol. An assay wavelength was 257 nm, a mobile phase was a mixed solution of acetonitrile and water (volume ratio: 40:60), and an octadecylsilylated column was used.

TABLE 1

| Classes | Components | Formulation 1 Content (mg) | Formulation 1 Content ratio (%) | Formulation 2 Content (mg) | Formulation 2 Content ratio (%) |
|---|---|---|---|---|---|
| Pharmacologically active component | Cilostazol | 200 | 36.36 | 200 | 30.76 |
| Release-controlling polymers | Carbomer | 100 | 18.19 | 100 | 15.38 |
|  | Hydroxypropyl methylcellulose (100,000 cps) | 100 | 18.19 | 200 | 30.76 |
| Binder | Povidone K-30 | 25 | 4.54 | 25 | 3.84 |
| Fillers | Microcrystalline cellulose | 100 | 18.19 | 100 | 15.38 |
|  | Light anhydrous silicic acid | 10 | 1.81 | 10 | 1.53 |
| Lubricant | Magnesium stearate | 15 | 2.72 | 15 | 2.35 |
| Total weight (based on one tablet) | | 550 | 100 | 650 | 100 |

TABLE 2

| | Elution rate (%) | |
|---|---|---|
| Time | Formulation 1 | Formulation 2 |
| 15 minutes | 3.8 | 1.9 |
| 30 minutes | 6.5 | 3.9 |
| 60 minutes | 9.4 | 8.2 |
| 90 minutes | 15.8 | 10.4 |
| 120 minutes | 20.4 | 15.9 |
| 240 minutes | 39.5 | 22.1 |
| 360 minutes | 58.2 | 35.2 |
| 480 minutes | 68.1 | 41.1 |
| 600 minutes | 72.1 | 52.6 |
| 720 minutes | 78.4 | 68.7 |
| 1,440 minutes | 92.8 | 89.1 |

Comparative Example 1

Formulations listed in the following Table 3 were prepared in the same manner as in Example 1, except that components listed in the following Table 3 were used.

TABLE 3

| Classes | Components | Formulation 3 Content (mg) | Formulation 3 Content ratio (%) | Formulation 4 Content (mg) | Formulation 4 Content ratio (%) | Formulation 5 Content (mg) | Formulation 5 Content ratio (%) |
|---|---|---|---|---|---|---|---|
| Pharmacologically active component | Cilostazol | 200 | 40 | 200 | 40 | 200 | 36.36 |
| Release-controlling polymers | Carbomer | — | — | 50 | 10 | 100 | 18.28 |
|  | Hydroxypropyl methylcellulose (4,000 cps) | — | — | 100 | 20 | 100 | 18.48 |
|  | Hydroxypropyl methylcellulose (100,000 cps) | 150 | 30 | — | — | — | — |
| Binder | Povidone K-30 | 25 | 5 | 25 | 5 | 25 | 4.55 |
| Fillers | Microcrystalline cellulose | 100 | 20 | 100 | 20 | 100 | 18.18 |
|  | Light anhydrous silicic acid | 10 | 2 | 10 | 2 | 10 | 1.82 |
| Lubricant | Magnesium stearate | 15 | 3 | 15 | 3 | 15 | 2.73 |
| Total weight (based on one tablet) | | 500 | 100 | 500 | 100 | 550 | 100 |

TABLE 4

| | Elution rate (%) | | |
|---|---|---|---|
| Time | Formulation 3 | Formulation 4 | Formulation 5 |
| 15 minutes | 4.1 | 8.9 | 7.4 |
| 30 minutes | 7.2 | 18.2 | 15.8 |
| 60 minutes | 10.4 | 34.7 | 30.7 |
| 90 minutes | 22.8 | 48.7 | 45.8 |
| 120 minutes | 31.4 | 59.6 | 60.7 |
| 240 minutes | 42.8 | 78.7 | 75.8 |
| 360 minutes | 68.7 | 85.8 | 86.2 |
| 480 minutes | 79.2 | 95.7 | 93.4 |
| 600 minutes | 95.7 | — | 99.8 |
| 720 minutes | 99.8 | — | — |

Example 2

Formulations listed in the following Table 5 were prepared in the same manner as in Example 1, except that components listed in the following Table 5 were used.

TABLE 5

| Classes | Components | Formulation 6 Content (mg) | Formulation 6 Content ratio (%) | Formulation 7 Content (mg) | Formulation 7 Content ratio (%) | Formulation 8 Content (mg) | Formulation 8 Content ratio (%) | Formulation 9 Content (mg) | Formulation 9 Content ratio (%) |
|---|---|---|---|---|---|---|---|---|---|
| Pharmacologically active component | Cilostazol | 200 | 40 | 200 | 38.46 | 200 | 42.55 | 200 | 33.33 |
| Release-controlling polymers | Carbomer | 50 | 10 | 70 | 13.46 | 10 | 4.25 | 50 | 8.33 |
|  | Hydroxypropyl methylcellulose (100,000 cps) | 100 | 20 | 100 | 19.23 | 100 | 21.28 | 200 | 33.33 |
| Binder | Povidone K-30 | 25 | 5 | 25 | 4.8 | 25 | 5.32 | 25 | 4.17 |
| Fillers | Microcrystalline cellulose | 100 | 20 | 100 | 19.23 | 100 | 21.28 | 100 | 16.67 |
|  | Light anhydrous silicic acid | 10 | 2 | 10 | 1.92 | 10 | 2.13 | 10 | 1.67 |
| Lubricant | Magnesium stearate | 15 | 3 | 15 | 2.88 | 15 | 3.19 | 15 | 2.5 |
| Total weight (based on one tablet) |  | 500 | 100 | 520 | 100 | 470 | 100 | 600 | 100 |

TABLE 6

| Time | Elution rate (%) Formulation 6 | Formulation 7 | Formulation 8 | Formulation 9 |
|---|---|---|---|---|
| 15 minutes | 4.5 | 5.2 | 4.8 | 2.1 |
| 30 minutes | 7.6 | 8.1 | 8.0 | 5.4 |
| 60 minutes | 11.8 | 12.3 | 10.9 | 8.7 |
| 90 minutes | 15.9 | 16.8 | 13.8 | 10.9 |
| 120 minutes | 22.3 | 23.4 | 22.4 | 15.8 |
| 240 minutes | 26.8 | 29.8 | 31.2 | 21.3 |
| 360 minutes | 38.2 | 40.1 | 45.3 | 31.2 |
| 480 minutes | 41.1 | 45.2 | 46.8 | 40.8 |
| 600 minutes | 52.8 | 50.8 | 58.2 | 48.2 |
| 720 minutes | 68.2 | 61.7 | 79.2 | 59.8 |
| 1,440 minutes | 100.5 | 98.2 | 100.8 | 95.2 |

Example 3

Formulations listed in the following Table 7 were prepared in the same manner as in Example 1, except that components listed in the following Table 7 were used.

TABLE 7

| Classes | Components | Formulation 10 Content (mg) | Formulation 10 Content ratio (%) | Formulation 11 Content (mg) | Formulation 11 Content ratio (%) | Formulation 12 Content (mg) | Formulation 12 Content ratio (%) | Formulation 13 Content (mg) | Formulation 13 Content ratio (%) |
|---|---|---|---|---|---|---|---|---|---|
| Pharmacologically active component | Cilostazol | 200 | 32.26 | 200 | 42.56 | 200 | 36.37 | 200 | 33.33 |
| Release-controlling polymers | Carbomer | 70 | 11.30 | 20 | 4.26 | 50 | 9.09 | 100 | 16.67 |
|  | Hydroxypropyl methylcellulose (100,000 cps) | 200 | 32.26 | 100 | 21.28 | 150 | 27.28 | 150 | 25 |
| Binder | Povidone K-30 | 25 | 4.03 | 25 | 5.31 | 25 | 4.54 | 25 | 4.16 |
| Fillers | Microcrystalline cellulose | 100 | 16.12 | 100 | 21.28 | 100 | 18.19 | 100 | 16.67 |
|  | Light anhydrous silicic acid | 10 | 1.61 | 10 | 2.12 | 10 | 1.81 | 10 | 1.67 |
| Lubricant | Magnesium stearate | 15 | 2.42 | 15 | 3.19 | 15 | 2.72 | 15 | 2.5 |
| Total weight (based on one tablet) |  | 620 | 100 | 470 | 100 | 550 | 100 | 600 | 100 |

TABLE 8

| Time | Elution rate (%) | | | |
|---|---|---|---|---|
| | Formulation 10 | Formulation 11 | Formulation 12 | Formulation 13 |
| 15 minutes | 3.2 | 2.1 | 3.4 | 3.7 |
| 30 minutes | 6.8 | 4.2 | 5.9 | 6.1 |
| 60 minutes | 10.1 | 6.8 | 8.2 | 9.8 |
| 90 minutes | 13.8 | 10.7 | 12.1 | 12.4 |
| 120 minutes | 20.9 | 18.1 | 19.8 | 18.7 |
| 240 minutes | 22.8 | 20.3 | 21.3 | 21.4 |
| 360 minutes | 34.2 | 31.2 | 33.8 | 33.2 |
| 480 minutes | 39.8 | 35.8 | 36.7 | 41.2 |
| 600 minutes | 50.1 | 48.1 | 49.2 | 52.8 |
| 720 minutes | 63.9 | 57.2 | 61.8 | 65.7 |
| 1,440 minutes | 96.8 | 94.9 | 97.2 | 100.8 |

Example 4

Formulations listed in the following Table 9 were prepared in the same manner as in Example 1, except that components listed in the following Table 9 were used.

TABLE 9

| Classes | Components | Formulation 14 | | Formulation 15 | | Formulation 16 | | Formulation 17 | |
|---|---|---|---|---|---|---|---|---|---|
| | | Content (mg) | Content ratio (%) | Content (mg) | Content ratio (%) | Content (mg) | Content ratio (%) | Content (mg) | Content ratio (%) |
| Pharmacologically active component | Cilostazol | 200 | 42.56 | 200 | 42.56 | 200 | 42.56 | 200 | 42.56 |
| Release-controlling polymers | Hydroxypropyl cellulose | 20 | 4.25 | — | — | — | — | — | — |
| | Methylcellulose | — | — | 20 | 4.25 | — | — | — | — |
| | Povidone K-90 | — | — | — | — | 20 | 4.25 | — | — |
| | Polyvinyl alcohol | — | — | — | — | — | — | 20 | 4.25 |
| | Hydroxypropyl methylcellulose (100,000 cps) | 100 | 21.28 | 100 | 21.28 | 100 | 21.28 | 100 | 21.28 |
| Binder | Povidone K-30 | 25 | 5.31 | 25 | 5.31 | 25 | 5.31 | 25 | 5.31 |
| Fillers | Microcrystalline cellulose | 100 | 21.28 | 100 | 21.28 | 100 | 21.28 | 100 | 21.28 |
| | Light anhydrous silicic acid | 10 | 2.12 | 10 | 2.12 | 10 | 2.12 | 10 | 2.12 |
| Lubricant | Magnesium stearate | 15 | 3.20 | 15 | 3.20 | 15 | 3.20 | 15 | 3.20 |
| Total weight (based on one tablet) | | 470 | 100 | 470 | 100 | 470 | 100 | 470 | 100 |

TABLE 10

| Time | Elution rate (%) | | | |
|---|---|---|---|---|
| | Formulation 14 | Formulation 15 | Formulation 16 | Formulation 17 |
| 15 minutes | 3.9 | 4.1 | 4.3 | 3.2 |
| 30 minutes | 6.9 | 5.8 | 6.1 | 4.9 |
| 60 minutes | 12.5 | 12.9 | 10.9 | 8.2 |
| 90 minutes | 15.1 | 16.4 | 15.8 | 14.8 |
| 120 minutes | 20.9 | 22.3 | 20.4 | 19.9 |
| 240 minutes | 25.4 | 26.9 | 25.4 | 24.8 |
| 360 minutes | 37.1 | 35.7 | 38.2 | 36.1 |
| 480 minutes | 40.6 | 41.2 | 43.8 | 41.5 |
| 600 minutes | 48.2 | 46.2 | 47.9 | 41.0 |
| 720 minutes | 70.1 | 72.9 | 70.8 | 73.1 |
| 1,440 minutes | 99.8 | 99.5 | 99.2 | 98.9 |

Example 5

The formulations 6, 7, 8 and 9 of the slow-release cilostazol tablets prepared in Examples 1 to 4 were used to perform elution tests according to changes in pH. An aqueous solution of 0.5 W/W % sodium lauryl sulfate (pH 1.2 (e.g., an artificial gastric juice) and pH 6.8 (e.g., an artificial intestinal juice) described in the elution test method of Korean Herbal Pharmacopoeia was used as an elution solution, and a paddle method was used as an elution method. In this case, the elution method was performed at a stirring speed of 75 rpm and an elution temperature of 37±0.5° C. in 900 ml of an elution solution. A sampling time was set based on a time required for a tablet to stay in the stomach when taking the tablet. Then, the samples were subjected to the elution test (pH 1.2), followed by performing the elution test (pH 6.8). 5 ml of each sample was taken and an equivalent amount of an elution solution was added to each sample. The analysis conditions were as follows. The solutions obtained from the elution test were filtered through a 0.45 μm membrane filter, and the resulting filtrates were quantified by HPLC using cilostazol. An assay wavelength was 257 nm, a mobile phase was a mixed solution of acetonitrile and water (volume ratio: 40:60), and an octadecylsilylated column was used.

TABLE 11

| | Elution rate (%) | | | | Elution rate (%) | | | |
|---|---|---|---|---|---|---|---|---|
| | Formulation 6 | | Formulation 7 | | Formulation 8 | | Formulation 9 | |
| Time | pH 1.2 | pH 6.8 | pH 1.2 | pH 6.8 | pH 1.2 | pH 6.8 | pH 1.2 | pH 6.8 |
| 15 minutes | 5.2 | — | 5.4 | — | 5.5 | — | 3.2 | — |
| 30 minutes | 8.2 | — | 9.3 | — | 8.9 | — | 5.7 | — |
| 60 minutes | 12.1 | — | 13.2 | — | 12.3 | — | 9.2 | — |
| 90 minutes | 16.8 | — | 16.9 | — | 15.9 | — | 12.9 | — |
| 120 minutes | 24.9 | — | 25.7 | — | 24.8 | — | 18.9 | — |
| 240 minutes | — | 29.2 | — | 32.9 | — | 32.9 | — | 22.6 |
| 360 minutes | — | 39.1 | — | 41.2 | — | 46.9 | — | 33.1 |
| 480 minutes | — | 42.8 | — | 48.6 | — | 48.9 | — | 41.9 |
| 600 minutes | — | 55.1 | — | 52.1 | — | 55.9 | — | 51.0 |
| 720 minutes | — | 68.7 | — | 62.7 | — | 73.2 | — | 62.8 |

What is claimed is:

1. A slow-release cilostazol tablet comprising cilostazol, a release-controlling polymer, a binder, a filler and a lubricant, wherein the release-controlling polymer is a 1.5:1 to 20:1 mixture of hydroxypropyl methylcellulose having a viscosity of 80,000 cps to 120,000 cps and a carbomer, wherein the tablet does not comprise a coating comprising a release-controlling polymer, and wherein the tablet has the following elution profiles according to a paddle method of 37+0.5° C., 0.5 W/W % sodium lauryl sulfate solution, 75 rpm;
   (a) the tablet releases 1.9% to 4.8% of the cilostazol after 15 minutes;
   (b) the tablet releases 20.3% to 31.2% of the cilostazol after 240 minutes; and
   (c) the tablet releases 89.1% to 100.8% of the cilostazol after 1440 minutes.

2. The slow-release cilostazol tablet according to claim 1, wherein the mixture of the hydroxypropyl methylcellulose and the carbomer is included at a content of 25 to 50% by weight, based on the total weight of the tablet.

3. A slow-release cilostazol tablet comprising cilostazol, a release-controlling polymer, a binder, a filler, and a lubricant, wherein the release-controlling polymer is a mixture of hydroxypropyl methyl cellulose and a carbomer, and wherein the tablet is prepared by:
   a. mixing the cilostazol, hydroxyproplyl methylcellulose, carbomer, binder, and filler together to form a mixture, wherein the hydroxypropyl methylcelluose and carbomer are present in a ratio of 1.5:1 to 10:1;
   b. forming the mixture into wet granules;
   c. drying the wet granules in an oven to form dry granules;
   d. passing the dry granules through a sieve to form a sieved product;
   e. adding the lubricant to the sieved product; and
   f. forming the lubricant and sieved product into the tablet, and wherein the tablet does not comprise a coating comprising the release-controlling polymer, and wherein the tablet has the following elution profile according to a paddle method of 37+0.5° C., 0.5 W/W % sodium lauryl sulfate solution, 75 rpm;
   (a) the tablet releases 1.9% to 4.8% of the cilostazol after 15 minutes;
   (b) the tablet releases 20.3% to 31.2% of the cilostazol after 240 minutes; and
   (c) the tablet releases 89.1% to 100.8% of the cilostazol after 1440 minutes.

4. A slow-release cilostazol tablet comprising cilostazol, a release-controlling polymer, a binder, a filler and a lubricant, wherein the release-controlling polymer is a 1.5:1 to 10:1 mixture of hydroxypropyl methylcellulose having a viscosity of 80,000 cps to 120,000 cps and a carbomer, the tablet releases about 57% to 80% of the cilostazol after 12 hours and about 89% to 98% of the cilostazol after 24 hours, and wherein the tablet does not comprise a coating comprising the release-controlling polymer.

5. The slow-release cilostazol tablet according to claim 1, wherein the elution profile is characterized that:
   (a) the tablet releases 1.9% to 4.8% of the cilostazol after 15 minutes;
   (b) the tablet releases 10.4% to 15.9% of the cilostazol after 90 minutes;
   (c) the tablet releases 20.3% to 31.2% of the cilostazol after 240 minutes;
   (d) the tablet releases 48.1% to 58.2% of the cilostazol after 600 minutes; and
   (e) the tablet releases 89.1% to 100.8% of the cilostazol after 1440 minutes.

6. The slow-release cilostazol tablet according to claim 1, wherein the elution profile is characterized that:
   (a) the tablet releases 1.9% to 4.8% of the cilostazol after 15 minutes;
   (b) the tablet releases 6.8% to 11.8% of the cilostazol after 60 minutes;
   (c) the tablet releases 10.4% to 15.9% of the cilostazol after 90 minutes;
   (d) the tablet releases 20.3% to 31.2% of the cilostazol after 240 minutes;
   (e) the tablet releases 35.8% to 46.8% of the cilostazol after 480 minutes;
   (f) the tablet releases 48.1% to 58.2% of the cilostazol after 600 minutes; and
   (e) the tablet releases 89.1% to 100.8% of the cilostazol after 1440 minutes.

7. The slow-release cilostazol tablet according to claim 1, wherein the elution profile is characterized that:
   (a) the tablet releases 1.9% to 4.8% of the cilostazol after 15 minutes;
   (b) the tablet releases 3.9% to 8.0% of the cilostazol after 30 minutes;
   (c) the tablet releases 6.8% to 11.8% of the cilostazol after 60 minutes;
   (d) the tablet releases 10.4% to 15.9% of the cilostazol after 90 minutes;
   (e) the tablet releases 15.8% to 22.4% of the cilostazol after 120 minutes;
   (f) the tablet releases 20.3% to 31.2% of the cilostazol after 240 minutes;

(g) the tablet releases 31.2% to 45.3% of the cilostazol after 360 minutes;
(h) the tablet releases 35.8% to 46.8% of the cilostazol after 480 minutes;
(i) the tablet releases 48.1% to 58.2% of the cilostazol after 600 minutes;
(j) the tablet releases 57.2% to 79.2% of the cilostazol after 720 minutes; and
(k) the tablet releases 89.1% to 100.8% of the cilostazol after 1440 minutes.

* * * * *